(12) United States Patent
Jones et al.

(10) Patent No.: US 9,414,997 B2
(45) Date of Patent: Aug. 16, 2016

(54) BENEFIT DELIVERY PARTICLE, COMPOSITIONS COMPRISING SAID PARTICLES AND A METHOD FOR TREATING SUBSTRATES

(71) Applicant: Conopco, Inc., Englewood Cliffs, NJ (US)

(72) Inventors: Craig Warren Jones, Bebington (GB); Adam John Limer, Bebington (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/443,148

(22) PCT Filed: Nov. 13, 2013

(86) PCT No.: PCT/EP2013/073695
§ 371 (c)(1),
(2) Date: May 15, 2015

(87) PCT Pub. No.: WO2014/079745
PCT Pub. Date: May 30, 2014

(65) Prior Publication Data
US 2015/0272839 A1    Oct. 1, 2015

(30) Foreign Application Priority Data
Nov. 23, 2012  (EP) ..................... 12193981

(51) Int. Cl.
| | |
|---|---|
| A61Q 13/00 | (2006.01) |
| A61Q 15/00 | (2006.01) |
| A61Q 19/00 | (2006.01) |
| A61Q 5/02 | (2006.01) |
| A61K 8/02 | (2006.01) |
| A61K 8/73 | (2006.01) |
| A61K 8/81 | (2006.01) |
| A61Q 5/12 | (2006.01) |
| A61Q 19/10 | (2006.01) |
| C11D 3/50 | (2006.01) |
| C11D 17/00 | (2006.01) |

(52) U.S. Cl.
CPC ............ *A61K 8/0245* (2013.01); *A61K 8/0241* (2013.01); *A61K 8/73* (2013.01); *A61K 8/737* (2013.01); *A61K 8/8152* (2013.01); *A61Q 5/02* (2013.01); *A61Q 5/12* (2013.01); *A61Q 13/00* (2013.01); *A61Q 15/00* (2013.01); *A61Q 19/00* (2013.01); *A61Q 19/10* (2013.01); *C11D 3/505* (2013.01); *C11D 17/0039* (2013.01); *A61K 2800/412* (2013.01); *A61K 2800/54* (2013.01); *A61K 2800/56* (2013.01); *A61K 2800/624* (2013.01); *A61K 2800/63* (2013.01)

(58) Field of Classification Search
CPC .................. A61K 2800/412; A61K 2800/54; A61K 2800/56; A61K 2800/624; A61K 2800/63; A61K 8/0241; A61K 8/0245; A61K 8/73; A61K 8/737; A61K 8/8152; A61Q 13/00; A61Q 15/00; A61Q 19/00; A61Q 19/10; A61Q 5/02; A61Q 5/12; C11D 17/0039; C11D 3/505
See application file for complete search history.

(56) References Cited

U.S. PATENT DOCUMENTS

| | | |
|---|---|---|
| 3,429,827 A | 2/1969 | Ruus |
| 5,290,858 A | 3/1994 | Sasaki |
| 5,726,138 A | 3/1998 | Tsaur |
| 6,734,299 B1 | 5/2004 | Clark |
| 7,867,968 B1 | 1/2011 | Aouad |
| 2003/0018102 A1 | 1/2003 | Weston |
| 2003/0068495 A1 | 4/2003 | Ferguson |
| 2004/0071742 A1 | 4/2004 | Popplewell |
| 2004/0072719 A1 | 4/2004 | Bennett |
| 2004/0139554 A1 | 7/2004 | Ferguson |
| 2004/0253376 A1 | 12/2004 | Parker |
| 2005/0276831 A1 | 12/2005 | Dihora |
| 2006/0039934 A1 | 2/2006 | Ness |
| 2006/0051425 A1 | 3/2006 | Kvitnitsky |
| 2006/0188582 A1 | 8/2006 | Naylor Da Rocha Gomes |
| 2006/0258557 A1 | 11/2006 | Popplewell |
| 2007/0071978 A1 | 3/2007 | Sojka |
| 2007/0111002 A1 | 5/2007 | Xia |
| 2007/0138672 A1 | 6/2007 | Lee |
| 2008/0081175 A1 | 4/2008 | Mukkamala |

(Continued)

FOREIGN PATENT DOCUMENTS

| | | |
|---|---|---|
| EP | 1321136 | 6/2003 |
| EP | 1479432 | 6/2007 |

(Continued)

OTHER PUBLICATIONS

Schneider et al. (Nano Letters 2009;9(2):636-642).*

(Continued)

*Primary Examiner* — Ernst V Arnold
(74) *Attorney, Agent, or Firm* — Rimma Mitelman

(57) ABSTRACT

A particle comprising: a core, comprising an optional benefit agent; an inner shell at least partially surrounding the core, the inner shell being the water insoluble product of a polymerization reaction to form a first polymer with a glass transition temperature above and including 70 degrees Celsius, preferably above and including 80 degrees Celsius; an outer shell at least partially surrounding the inner shell, the outer shell being the water insoluble product of a polymerization reaction to form a second polymer with a glass transition temperature below and including 35 degrees Celsius; and a deposition aid, covalently attached to the outer shell.

17 Claims, No Drawings

(56) References Cited

U.S. PATENT DOCUMENTS

| | | |
|---|---|---|
| 2008/0146478 A1 | 6/2008 | Lei |
| 2008/0311064 A1 | 12/2008 | Lei et al. |
| 2009/0155371 A1 | 6/2009 | Sojka |
| 2009/0275494 A1 | 11/2009 | Ferguson |
| 2009/0289216 A1 | 11/2009 | Jung |
| 2009/0312222 A1 | 12/2009 | Ferguson et al. |
| 2010/0168251 A1 | 7/2010 | Warr |
| 2010/0216684 A1 | 8/2010 | Ferguson |
| 2010/0291197 A1 | 11/2010 | Schwab |
| 2010/0311637 A1 | 12/2010 | Alonso |
| 2011/0008427 A1 | 1/2011 | Biggs |
| 2011/0082066 A1 | 4/2011 | Wrubbel |
| 2011/0104218 A1 | 5/2011 | Karles |
| 2011/0152159 A1 | 6/2011 | Labeque |
| 2011/0177993 A1 | 7/2011 | Mort |
| 2012/0015010 A1 | 1/2012 | Cummins |
| 2013/0017395 A1 | 1/2013 | Zhou et al. |
| 2013/0122070 A1 | 5/2013 | Barnett et al. |

FOREIGN PATENT DOCUMENTS

| | | |
|---|---|---|
| EP | 1954793 | 4/2009 |
| EP | 2554630 | 2/2013 |
| GB | 2432851 | 6/2007 |
| GB | 2432852 | 6/2007 |
| HU | 9903296 | 5/2001 |
| IN | 01628DE2004 | 3/2009 |
| JP | 2008273881 | 11/2008 |
| JP | 2009215475 | 9/2009 |
| TW | 209871 | 7/1993 |
| WO | WO9629979 | 10/1996 |
| WO | WO0068352 | 11/2000 |
| WO | WO2009134234 | 11/2009 |
| WO | WO2011158962 | 12/2011 |
| WO | WO2012007438 | 1/2012 |
| WO | WO2012022034 | 2/2012 |
| WO | WO2012038144 | 3/2012 |
| WO | WO2013107586 | 7/2013 |
| ZA | 9602367 | 9/1997 |

OTHER PUBLICATIONS

Search Report in PCTEP2013073695, Aug. 19, 2014.
Written Opinion in PCTEP2013073695, Aug. 19, 2014.

* cited by examiner

BENEFIT DELIVERY PARTICLE, COMPOSITIONS COMPRISING SAID PARTICLES AND A METHOD FOR TREATING SUBSTRATES

TECHNICAL FIELD

The present invention relates to a particle, comprising shells having different thermal transition (Tg) properties, a deposition aid and optionally a benefit agent. These particles are useful in a wide range of home and personal care compositions, with particular relevance to compositions that are used in an aqueous environment comprising a rinse, for the treatment of textiles, hair and skin.

BACKGROUND

Many home and personal care formulations seek to deliver so-called benefit agents to substrates such as cloth, hair and skin. Encapsulation of the benefit agent in particles has been proposed as a means of enhancing delivery, which is advantageous because of the expense of some benefit agents. Delivery of particles per se can also be useful where the particles, even in the absence of specific benefit agents, confer a benefit.

These particles may comprise polymers and many different types of polymerisation are known. In the present specification a distinction will be drawn between step-growth and chain-growth polymerisation. This is the well-established reaction mechanism distinction drawn by Paul Flory in 1953 (see Paul J. Flory, "Principles of Polymer Chemistry", Cornell University Press, 1953, p. 39. ISBN 0801401348).

For the purposes of the present specification a chain-growth polymer is a polymer which is formed by a reaction in which monomers bond together via rearrangement (for example, of unsaturated and typically vinyllic bonds, or by a ring-opening reaction) without the loss of any atom or molecule. Chain-growth polymers grow in a single direction from one end of the chain only and an initiator is typically used. In chain-growth polymerisation it is commonplace that once a growth at a chain end is terminated the end becomes unreactive.

An example of one type of chain-growth polymerisation is the free-radical polymerisation reaction, for example the well-known polymerization of styrene (vinyl benzene) in the presence of benzoyl peroxide (as radical initiator) to produce polystyrene. Similarly, aluminum chloride may be used to initiate the polymerisation of isobutylene to form synthetic rubber. Other examples include the polymerization reactions of acrylates or methacryates.

A step-growth polymer is a polymer whose chain is formed during by the reaction of poly-functional monomers to form increasingly larger oligomers. Growth occurs throughout the matrix and the monomer level falls rapidly in the early stages of the reaction. No initiator is needed for a step growth polymerisation and the ends of the growing chain generally remain active at all times. Typically (but not always) a small molecule, which is often water, is eliminated in the polymerization process.

An example of step-growth polymerization is the formation of polyester by the reaction of dicarboxylic acids and glycols with elimination of water. Another example is the polymerisation of phenol and formaldehyde to produce "Bakelite". Other well known step-growth polymerisation reactions are the formation of polyesters, polyurethanes, polyureas, polyamides and polyethers.

Both chain-growth and step-growth have been used to prepare particles by polymerisation in which some of the components are present in the dispersed phase of an emulsion. In the case of chain-growth, all of the components may be present in droplets of the dispersed phase which, once initiated, react internally to form a particle. In the case of step-growth, components may be present both in the dispersed and the continuous phase to react at the dispersed phase surface to form a "shell" at the interface.

In US 2009/312222 particles are prepared using so-called "mini-emulsion" polymerisation, to give a particle with a size as from about 30 to 500 nm. The polymer comprises units derived from monomers that are capable of undergoing chain-growth free-radical polymerisation. GB 2432851 discloses particles derived from monomers that are capable of undergoing free-radical polymerisation. GB 2432850 discloses core/shell particles in which both the core and the shell comprises monomer units which are derived from monomers that are capable of undergoing free-radical polymerisation.

Emulsion polymerisation can also be performed using step-growth reactions. U.S. Pat. No. 4,622,267 discloses an interfacial polymerization technique for preparation of microcapsules. US 2002/169233 discloses an interfacial polymerization process wherein a microcapsule wall of a polyamide, an epoxy resin, a polyurethane, a polyurea or the like is formed at an interface between two phases. The core material is initially dissolved in a solvent and an aliphatic diisocyanate soluble in the solvent mixture is added. Subsequently, a non-solvent for the aliphatic diisocyanate is added until the turbidity point is just barely reached. This organic phase is then emulsified in an aqueous solution, and a reactive amine is added to the aqueous phase. The amine diffuses to the interface, where it reacts with the diisocyanate to form polymeric polyurea shells.

Microcapsules have been proposed in which the wall material comprises both a step-growth polymer and a chain-growth polymer.

US 2005/0153839 disclose microcapsules for use in the production of multicolour thermo-sensitive recording materials having polyurethane or polyurea walls. The polymer wall includes (via a covalent bond) a polymer obtained by radically polymerising at least a vinyl monomer further comprising a polyether. Preferably the raw materials for the walls are di-isocyanates. It should be noted that the vinyl polymer is included in the wall rather than being enclosed by it.

EP 2204155 discloses leak-proof, friable core-shell fragrance microcapsules which have melamine-formaldehyde (step-growth polymer) shells and in which the core may optionally comprise, among other possibilities, high density organic oil-soluble ingredients which may be prepared by any standard means such as radical polymerisation of unsaturated monomers such as vinyl or acrylic monomers (which are chain-growth polymers). Alternatively the polymers may be prepared by condensation reactions such as those leading to polyethers or polyesters (which are step-growth polymers). The fragrance comprises at least one cyclic fragrance material. The reason for including these pre-formed high density materials is to match the density of the micro-capsules with that of the composition in which they are used, to prevent separation.

Our co-pending case, having the application number EP 12 151460.8, describes a personal care composition, preferably for use on human skin and/or hair, including a core-shell benefit agent carrier particle comprising: a) a core, optionally comprising a benefit agent; b) at least one polymer shell surrounding the core, c) a deposition aid, attached to the outer shell and not removed by exposure to water, said deposition aid comprising at least one polysaccharide selected from the group consisting of poly-mannan, poly-glucan, poly-glucomannan, poly-xyloglucan, poly-galactomannan, dextran, hydroxyl-propyl cellulose, hydroxy-propyl methyl cellulose, hydroxy-ethyl methyl cellulose, hydroxy-propyl guar, hydroxy-ethyl ethyl cellulose or methyl cellulose, with the proviso that the particle is not a particle having an average diameter of less than 50 micron comprising; i) at least one shell formed by a step-growth polymerisation reaction, ii) interior to said shell, at least one region formed by chain-growth polymerisation reaction which does not involve an isocyanate, wherein the shell is polymerised prior to the core.

BRIEF DESCRIPTION OF THE INVENTION

In a first aspect, the present invention provides a particle comprising:
 a) a core, comprising an optional benefit agent;
 b) an inner shell at least partially surrounding the core, said inner shell being the water insoluble product of a polymerisation reaction to form a first polymer with a glass transition temperature above and including 70 degrees Celsius, preferably above and including 80 degrees Celsius;
 c) an outer shell at least partially surrounding said inner shell, said outer shell being the water insoluble product of a polymerisation reaction to form a second polymer with a glass transition temperature below and including 35 degrees Celsius, wherein the second polymer is formed from a monomer having a solubility in water of greater than 3 g/L at STP; and
 d) a deposition aid, covalently attached to the outer shell.

A second aspect of the invention provides a process for the manufacture of a product comprising the particles according to the first aspect of the invention wherein the particles and the benefit agent are added separately to the formulation.

A further aspect of the present invention provides a method of treatment of a substrate, preferably wherein the substrate is selected from skin and/or hair, which includes the step of treating the substrate with a composition comprising particles according to the first aspect of the invention.

A yet further aspect of the present invention provides a home or personal care composition comprising at least one particle according to the first aspect of the invention, more preferably a deodorant, antiperspirant, shampoo, hair conditioner or skin care or skin cleansing product.

DETAILED DESCRIPTION OF THE INVENTION

In order that the present invention may be further and better understood it will be further described below with reference to specific embodiments of the invention and further preferred and/or optional features. All amounts quoted are wt. % of total composition unless otherwise stated.

Except in the operating and comparative examples, or where otherwise explicitly indicated, all numbers in this description indicating amounts or ratios of material or conditions of reaction, physical properties of materials and/or use are to be understood as modified by the word "about".

The Particle

The particle of the invention have an inner region, forming the "core", which may provide a sink for a benefit agent and an inner "glassy shell" which protects the benefit agent and regulates the flow of benefit agent into and out of the core. An outer shell at least surrounds the inner shell and a deposition aid is covalently attached to the outer shell. Thus, the particle can be a carrier which controls thermodynamic (rather than kinetic) partition of a benefit agent between the interior region and elsewhere. This is particularly advantageous where late-stage addition of benefit agent, such as perfume, is required as the particles and the perfume may be dosed into the product separately.

Typically, the particle has an average diameter of less than 10 micron, and preferably an average diameter of less than 1 micron, more preferably less than 500 nm. One benefit of small particles is that they are less visible in clear products. Another useful benefit is that sizes below 500 nm favour deposition on fibrous substrates and can allow formulation without the need for suspending and/or structuring systems. Most typically the particles are in the size range of 50-500 nm, preferably 100-300 nm, the size being controllable by the presence of surfactant in the polymerisation mixture.

As the particles of the present invention can be small, especially below 500 nm, they do not require suspending agents and thereby simplify product formulation and enable the production of clear/transparent products. Mini-emulsion particles can be a small as 50 nm.

The Core

The core may be formed by a chain-growth polymerisation reaction, which is a radical polymerisation reaction, more preferably of at least one ethylenically unsaturated monomer, conveniently a vinylic monomer, most preferably selected from acrylate or methacrylate. Such materials enable the compatibility of the core and optional benefit agent to be optimised for desirable delivery parameters. In particular the solubility parameters of the optional benefit agent and the chain-growth polymer comprising the core may be matched to achieve improved absorption and/or delivery.

Preferably the core of the particle is a rubbery material, i.e. one which has a Tg such that it is rubbery under conditions of storage. Suitable materials are the C2-C30, preferably C3 to C18, more preferably C3 to C12 acrylates or methacrylates, with C3 to C8, linear or branched acrylates and methacrylates being particularly preferred, for example butyl-, hexyl- and ethylhexyl-acrylates and methacrylates. Where a benefit agent is present, the core is intended to be a solvent for the benefit agent.

The Inner Shell

The particle comprises an inner shell, which at least partially surrounds the core, preferably substantially surrounds the core and most preferably fully surrounds the core. (At lower monomer levels, the shell may not be fully formed around the core.)

The inner shell is the water insoluble product of a polymerisation reaction to form a first polymer with a glass transition temperature above and including 70 degrees Celsius, preferably above and including 80 degrees Celsius. A preferred range is from 70 to 120 Celcius, more preferably from 80 to 115 Celcius and most preferably from 90 to 110 Celcius.

Preferably the inner shell of the particle is a glassy material, i.e. one which has a Tg such that it is glassy under the conditions of storage. Suitable materials are methyl methacrylates. The shell is intended to be a kinetic barrier for the benefit agent as well as maintaining capsule integrity. Typically the shell is 10-100 nm thick, preferably 20-40 nm.

The inner shell may be formed by step-growth polymerisation, which is not a condensation polymerisation, and, more preferably, involves an isocyanate monomer, more preferably a urethane and/or a urea. Isocyanate monomers are reactive, enable high monomer conversion, and form a robust, glassy shell which can survive drying and other processing. Isocyanate monomers react by a step-growth mechanism but are categorised as an addition polymer by virtue of no small molecule being eliminated during polymerisation.

Alternatively, the inner shell may be formed by chain-growth polymerisation.

The Outer Shell

The particle comprises an outer shell at least partially surrounding said inner shell.

The outer shell is the water insoluble product of a polymerisation reaction to form a second polymer with a glass transition temperature below and including 35 Celcius, preferably from minus 55 to +35 Celcius, more preferably from minus 50 to +25 Celcius, even more preferably from minus 30 to +20 Celcius, most preferably from minus 30 to +15 Celcius.

The outer shell of the particle is a rubbery material, i.e. one which has a Tg such that it is rubbery under conditions of storage. Suitable materials are the C1-C30, preferably C1-C18, more preferably C1-C12 acylates or methacrylates, with the butyl and methyl derivatives being particularly preferred, most preferably methyl methacrylate.

The second polymer is formed from a monomer having a solubility in water of greater than 3 g/L at STP, preferably greater than and including 10 g/L, more preferably greater than and including 15 g/L. A preferred range of solubility in water is from 10 g/L to 100 g/L, more preferably from 15 g/L to 70 g/L and most preferably from 15 g/L to 60 g/L at STP (Standard Temperature and Pressure).

The second polymer needs to be hydrophobic enough to cause the deposition aid to interact with the particle.

The second polymer is present in an amount of preferably from 0.5 to 15 wt %, more preferably from 1 to 10 wt % even more preferably from 3 to 7.5 wt %, and most preferably from 4 to 6 wt % by weight of the total particle.

The Deposition Aid

The particle comprises a deposition aid. In particularly preferred embodiments the deposition aid is substantive to proteinaceous, cellulosic, polyester, lipid or polyamide surfaces. By use of such a deposition aid, the efficiency of delivery to a specific substrate may be enhanced.

The deposition aid is substantive to surfaces, for example skin and hair. By use of such a deposition aid, the efficiency of delivery to skin and hair may be enhanced. "Care" as used in the claims of the present specification is intended to include cleaning as well as conditioning, moisturising and other treatments of the skin and or hair.

The deposition aid is covalently bound to the outer shell. Thus the deposition aid should not be removed by exposure to water.

Deposition aids modify the properties of the exterior of the particle. One particular benefit which can be obtained with these materials is to make the particle more substantive to a desired substrate. Desired substrates include cellulosics (including cotton), polyesters (including those employed in the manufacture of polyester fabrics) and protein-containing substrates (such as akin and hair). Deposition aids are preferably selected from non-hydrolysable substrate-substantive polymers, hydrolysable substrate-substantive polymers and polyester-substantive polymers.

Preferred polysaccharide polymers, whether hydrolysable or not may be derived from a broad range of polysaccharides. Preferably, the polysaccharide is selected from the group consisting of: tamarind gum (preferably consisting of xyloglucan polymers), guar gum, locust bean gum (preferably consisting of galactomannan polymers), and other industrial gums and polymers, which include, but are not limited to, Tara, Fenugreek, Aloe, Chia, Flaxseed, *Psyllium* seed, quince seed, xanthan, gellan, welan, rhamsan, dextran, curdlan, pullulan, scleroglucan, schizophyllan, chitin, hydroxyalkyl cellulose, arabinan (preferably from sugar beets), de-branched arabinan (preferably from sugar beets), arabinoxylan (preferably from rye and wheat flour), galactan (preferably from lupin and potatoes), pectic galactan (preferably from potatoes), galactomannan (preferably from carob, and including both low and high viscosities), glucomannan, lichenan (preferably from icelandic moss), mannan (preferably from ivory nuts), pachyman, rhamnogalacturonan, *acacia* gum, agar, alginates, carrageenan, chitosan, clavan, hyaluronic acid, heparin, inulin, cellodextrins, cellulose, cellulose derivatives and mixtures thereof.

Preferred non-hydrolysable substrate-substantive deposition aids include non-hydrolysable polysaccharides. The polysaccharide preferred for cotton substantivity for example has a β-1,4-linked backbone.

Preferably the polysaccharide is a cellulose, a cellulose derivative, or another β-1,4-linked polysaccharide having an affinity for cellulose, such as polymannan, polyglucan, polyglucomannan, polyxyloglucan and polygalactomannan or a mixture thereof. More preferably, the polysaccharide is selected from the group consisting of polyxyloglucan and polygalactomannan. Most preferably, the deposition aid is locust bean gum, xyloglucan, guar gum or mixtures thereof.

In one embodiment, the deposition aid is a polysaccharide which is substantive at least to cotton. In this embodiment, the deposition aid includes at least one polysaccharide selected from the group consisting of polymannan, polyglucan, polyglucomannan, polyxyloglucan, polygalactomannan, dextran, hydroxyl-propyl cellulose, hydroxy-propyl methyl cellulose, hydroxy-ethyl methyl cellulose, hydroxy-propyl guar, hydroxy-ethyl ethyl cellulose or methyl cellulose.

Preferred hydrolysable substrate-substantive deposition aids include hydrolysable polysaccharides. These comprise a polysaccharide which has been modified to render it more water soluble by means of a group covalently attached to the polysaccharide by means of hydrolysable bond. Preferred groups may for example be independently selected from one or more of acetate, propanoate, trifluoroacetate, 2-(2-hydroxy-l-oxopropoxy)propanoate, lactate, glycolate, pyruvate, crotonate, isovalerate cinnamate, formate, salicylate, carbamate, methylcarbamate, benzoate, gluconate, methanesulphonate, toluene, sulphonate, groups and hemiester groups of fumaric, malonic, itaconic, oxalic, maleic, succinic, tartaric, aspartic, glutamic, and malic acids.

Preferred amongst such hydrolysable deposition aids for cotton substantivity is cellulose mono acetate.

Suitable and preferred polyester-substantive deposition aids include phthalate containing polymers, more preferably a polymer having one or more nonionic hydrophilic components comprising oxyethylene, polyoxyethylene, oxypropylene or polyoxypropylene segments, and, one or more hydrophobic components comprising terephthalate segments. Typically, oxyalkylene segments of these deposition aids will have a degree of polymerization of from 1 to about 400, although higher levels can be used, preferably from 100 to about 350, more preferably from 200 to about 300.

One type of preferred deposition aid is a copolymer having random blocks of ethylene terephthalate and polyethylene oxide terephthalate.

Another preferred polymeric deposition aid is polyester with repeat units of ethylene terephthalate units contains 10-15% by weight of ethylene terephthalate units together with 90-80% by weight of polyoxyethylene terephthalate units, derived from a polyethylene glycol of average molecular weight 0.2 kD-40 kD.

Examples of this class of polymer include the commercially available material ZELCON 5126 (from DuPont) and MILEASE T (from ICI). Examples of related polymers can be found in U.S. Pat. No. 4,702,857.

Another preferred polymeric deposition aid is a sulfonated product of a substantially linear ester oligomer comprised of an oligomeric ester backbone of terephthaloyl and oxyalkyleneoxy repeat units and terminal moieties covalently attached to the backbone. These soil release agents are described fully in U.S. Pat. No. 4,968,451. Other suitable polymeric soil release agents include the terephthalate polyesters of U.S. Pat. No. 4,711,730, the anionic end-capped oligomeric esters of U.S. Pat. No. 4,721,580, and the block polyester oligomeric compounds of U.S. Pat. No. 4,702,857.

Preferred polymeric deposition aids also include the soil release agents of U.S. Pat. No. 4,877,896 which discloses anionic, especially sulfoaroyl, end-capped terephthalate esters.

Still another preferred deposition aid is an oligomer with repeat units of terephthaloyl units, sulfoisoterephthaloyl units, oxyethyleneoxy and oxy-1,2-propylene units. The repeat units form the backbone of the oligomer and are preferably terminated with modified isethionate end-caps. A particularly preferred deposition aid of this type comprises about one sulfoisophthaloyl unit, 5 terephthaloyl units, oxyethyleneoxy and oxy-1,2-propyleneoxy units in a ratio of from about 1.7 to about 1.8, and two end-cap units of sodium 2-(2-hydroxyethoxy)-ethanesulfonate. Said soil release agent also comprises from about 0.5% to about 20%, by weight of the oligomer, of a crystalline-reducing stabilizer, preferably selected from the group consisting of xylene sulfonate, cumene sulfonate, toluene sulfonate, and mixtures thereof.

The deposition aid may be straight or branched. The preferred molecular weight of the polymeric deposition aid is in the range of from about 5 kD to about 500 kD, preferably 10 kD-500 kD, more preferably 20 kD-300 kD.

Preferably, the deposition-aid polymer is present at levels such that the ratio polymer:particle solids is in the range 1:500-3:1, preferably 1:200-1:3.

Chain Growth Polymers

The core and the outer shell are formed by chain-growth polymerisation. In one embodiment, the inner shell may also be formed by chain-growth polymerisation.

Free-radical polymerisation (FRP) is a suitable method of chain-growth polymerisation. In FRP a mono-functional monomer is polymerised in the presence of free-radical initiator and, optionally, a chain transfer agent. Chain transfer agents can act to reduce the average molecular weight of the final polymer.

The use of a separate chain transfer agent and an initiator is preferred. However, some molecules can perform both these functions.

The free-radical initiator can be any molecule known to initiate free-radical polymerisation such as azo-containing molecules, persulfates, redox initiators, peroxides, benzyl ketones. These initiators may be activated via thermal, photolytic or chemical means. In the method of the present invention, thermal activation is preferred.

Examples of suitable initiators include but are not limited to 2,2'-azobisisobutyronitrile (AIBN), azobis(4-cyanovaleric acid), benzoyl peroxide, cumylperoxide, 1-hydroxy-cyclohexyl phenyl ketone, hydrogen peroxide/ascorbic acid.

So-called 'iniferters' such as benzyl-N,N-diethyldithiocarbamate can also be used.

In some cases, more than one initiator may be used.

The preferred initiators are: 2,2'-Azobis(2-methylbutyronitrile), 2,2'-Azobis(2,4-dimethyl valeronitrile), 1,1'-Azobis(cyclohexane-1-carbonitrile) and t-butyl hydro-peroxide/ascorbic acid as these minimise the production of unwanted bi-products.

Preferably, the residue of the initiator in a free-radical polymerisation comprises 0 to 5% w/w, preferably 0.01 to 5% w/w and especially 0.01 to 3% w/w, of the resulting copolymer based on the total weight of the monomers.

The chain transfer agent is preferably a thiol-containing molecule and can be either mono-functional or multi-functional. The agent may be hydrophilic, hydrophobic, amphiphilic, anionic, cationic, neutral or zwitterionic. The molecule can also be an oligomer containing a thiol moiety.

Suitable thiols include but are not limited to $C_2$-$C_{18}$ alkyl thiols such as dodecane thiol, thioglycolic acid, thioglycerol, cysteine and cysteamine. Thiol-containing oligomers may also be used such as oligo(cysteine) or an oligomer which has been post-functionalised to give a thiol group(s), such as oligoethylene glycolyl(di)thio glycollate. Xanthates, dithioesters, and dithiocarbonates may also be used, such as cumyl phenyldithioacetate.

Alternative chain transfer agents may be any species known to limit the molecular weight in a free-radical addition polymerisation. Thus the chain-transfer agent may also be a hindered alcohol, halocarbon, alkyl halide or a transition metal salt or complex, or similar free-radical stabiliser. Catalytic chain transfer agents such as those based on transition metal complexes such as cobalt bis(borondi-fluorodimethyl-glyoximate) may also be used.

More than one chain transfer agent may be used in combination.

The residue of the chain transfer agent may comprise 0 to 20 mole %, preferably 0 to 10 mole % and especially 0 to 3 mole %, of the copolymer (based on the number of moles of mono-functional monomer). In some cases, for example in the case of some so-called living polymerisation methods, a chain transfer agent is not required.

The monomers which are capable of chain-growth polymerisation, are preferably ethylenically unsaturated, more preferably vinylic. In the alternative, a ring-opening mechanism may be used.

Monomers for the chain-growth polymerisation may comprise any carbon-carbon unsaturated (or cyclic) compound which can form an addition polymer, e.g. vinyl and allyl compounds. The mono-functional monomer may be hydrophilic, hydrophobic, amphiphilic, anionic, cationic, neutral or zwitterionic in nature. Thus, the mono-functional monomer may be selected from but not limited to monomers such as vinyl acids, vinyl acid esters, vinyl aryl compounds, vinyl acid anhydrides, vinyl amides, vinyl ethers, vinyl amines, vinyl aryl amines, vinyl nitriles, vinyl ketones, and derivatives of the aforementioned compounds as well as corresponding allyl variants thereof.

Other suitable mono-functional monomers for the chain-growth polymer include hydroxyl-containing monomers and monomers which can be post-reacted to form hydroxyl groups, acid-containing or acid functional monomers, zwitterionic monomers and quaternised amino monomers.

Oligomeric or oligo-functionalised monomers may also be used, especially oligomeric(meth)acrylic acid esters such as mono(alk/aryl)(meth)acrylic acid esters of oligo[alkyleneglycol] or oligo[dimethylsiloxane] or any other mono-vinyl or allyl adduct of a low molecular weight oligomer. Mixtures of more than one monomer may also be used.

Preferred vinyl acids and derivatives thereof include (meth)acrylic acid and acid halides thereof such as (meth)acryloyl chloride.

Preferred vinyl acid esters and derivatives thereof include C1-20 alkyl(meth)acrylates (linear & branched) such as methyl(meth)acrylate, stearyl(meth)acrylate and 2-ethyl hexyl(meth)acrylate, aryl(meth)acrylates such as benzyl (meth)acrylate, tri(alkyloxy)silylalkyl(meth)acrylates such as trimethoxysilylpropyl(meth)acrylate and activated esters of (meth)acrylic acid such as N-hydroxysuccinamido(meth)acrylate. Vinyl aryl compounds and derivatives thereof include styrene, acetoxystyrene, styrene sulfonic acid, vinyl pyridine, vinylbenzyl chloride and vinyl benzoic acid. Vinyl acid anhydrides and derivatives thereof include maleic anhydride. Vinyl amides and derivatives thereof include (meth)acrylamide, N-vinyl pyrrolidone, N-vinyl formamide, (meth)acrylamidopropyl trimethyl ammonium chloride, [3-((meth)acrylamido)propyl]dimethyl ammonium chloride, 3-[N-(3-(meth)acrylamidopropyl)-N,N-dimethyl]aminopropane sulfonate, methyl(meth)acrylamidoglycolate methyl ether and N-isopropyl(meth)acrylamide.

Vinyl ethers and derivatives thereof include methyl vinyl ether. Vinyl amines and derivatives thereof include dimethylaminoethyl(meth)acrylate, diethylaminoethyl(meth)acrylate, diisopropylaminoethyl(meth)acrylate, mono-t-butylaminoethyl(meth)acrylate, morpholinoethyl(meth)acrylate and monomers which can be post-reacted to form amine groups, such as vinyl formamide. Vinyl aryl amines and derivatives thereof include vinyl aniline, vinyl pyridine, N-vinyl carbazole and vinyl imidazole. Vinyl nitriles and derivatives thereof include (meth)acrylonitrile. Vinyl ketones and derivatives thereof include acreolin.

Hydroxyl-containing monomers include vinyl hydroxyl monomers such as hydroxyethyl(meth)acrylate, hydroxy propyl(meth)acrylate, glycerol mono(meth)acrylate and sugar mono(meth)acrylates such as glucose mono(meth)acrylate. Monomers which can be post-reacted to form hydroxyl groups include vinyl acetate, acetoxystyrene and glycidyl(meth)acrylate. Acid-containing or acid functional monomers include (meth)acrylic acid, styrene sulfonic acid, vinyl phosphonic acid, vinyl benzoic acid, maleic acid, fumaric acid, itaconic acid, 2-(meth)acrylamido 2-ethyl propanesulfonic acid, mono-2-((meth)acryloyloxy)ethyl succinate and ammonium sulfatoethyl(meth)acrylate. Zwitterionic monomers include (meth)acryloyl oxyethylphosphoryl choline and betaines, such as [2-((meth)acryloyloxy)ethyl]dimethyl-(3-sulfopropyl)ammonium hydroxide. Quaternised amino monomers include (meth)acryloyloxyethyltri-(alk/aryl)ammonium halides such as (meth)acryloyloxyethyltrimethyl ammonium chloride.

Oligomeric (or polymeric) monomers include oligomeric (meth)acrylic acid esters such as mono(alk/aryl)oxyoligo-alkyleneoxide(meth)acrylates and mono(alk/aryl)oxyoligo-dimethyl-siloxane(meth)acrylates. These esters include monomethoxy oligo(ethyleneglycol)mono(meth)acrylate, monomethoxy oligo(propyleneglycol)mono(meth)acrylate, monohydroxy oligo(ethyleneglycol)mono(meth)acrylate and monohydroxy oligo(propyleneglycol)mono(meth)acrylate.

Further examples include vinyl or allyl esters, amides or ethers of pre-formed oligomers formed via ring-opening polymerisation such as oligo(caprolactam) or oligo-(caprolactone), or oligomers formed via a living polymerisation technique such as oligo(1,4-butadiene). The polymeric monomers are the same, save that the oligomers are polymers.

Macromonomers are generally formed by linking a polymerisable moiety, such as a vinyl or allyl group, to a pre-formed monofunctional polymer via a suitable linking unit such as an ester, an amide or an ether. Examples of suitable polymers include mono functional poly(akylene oxide) such as monomethoxy[poly(ethyleneoxide) or monomethoxy [poly-(propyleneoxide), silicones such as poly(dimethylsiloxane), polymers formed by ring-opening polymerisation such as poly(caprolactone) or poly(caprolactam) or monofunctional polymers formed via living polymerisation such as poly(1,4-butadiene).

Preferred macromonomers include monomethoxy[poly-(ethyleneglycol)]mono(methacrylate), monomethoxy[poly-(propyleneglycol)]mono(methacrylate), poly(dimethylsiloxane)monomethacrylate.

The corresponding allyl monomers to those listed above can also be used where appropriate.

More preferred monomers include: amide-containing monomers such as (meth)acrylamide, N,N'-dimethyl(meth)acrylamide, N and or N'-di(alkyl or aryl)(meth)acrylamide, N-vinyl pyrollidone, (meth)acrylamidopropyl trimethyl ammonium chloride, [3-(methacroylamino)propyl]dimethyl ammonium chloride, 3-[N-(3-methacrylamido-propyl)-N,N-dimethyl]-aminopropane sulfonate, 4-(2-acrylamido-2-methylpropyl-dimethylammonio)butanoate, methyl acrylamidoglycolate methyl ether and N-isopropyl-(meth)acrylamide; (meth)acrylic acid derivatives such as (meth)acrylic acid, (meth)acryoloyl chloride (or any halide), (alkyl/aryl)(meth)acrylate, oligo-functionalised monomers such as monomethoxy poly(ethyleneglycol)monomethacrylate or monomethoxy poly(propyleneglycol)mono(meth)acrylate, glycerol mono(meth)acrylate, glycidyl(meth)acrylate and sugar mono(meth)acrylates such as glucose mono(meth)acrylate; vinyl amines such as dimethylaminoethyl(meth)acrylate, diethylaminoethyl(meth)acrylate, t-butylamino (meth)acrylate, morpholinoethylmethacrylate, or vinyl aryl amines such as vinyl aniline, vinyl pyridine, N-vinyl carbazole, vinyl imidazole; vinyl aryl monomers such as styrene, vinyl benzyl chloride, vinyl toluene, α-methyl styrene, styrene sulfonic acid and vinyl benzoic acid; vinyl hydroxyl monomers such as hydroxyethyl(meth)acrylate, hydroxy propyl(meth)acrylate, glyceryl(meth)acrylate or monomers which can be post-functionalised into hydroxyl groups such as vinyl acetate or acetoxy styrene can also be used; acid-containing monomers such as (meth)acrylic acid, styrene sulfonic acid, vinyl phosphonic, maleic acid, fumaric acid, itaconic acid, 2-acrylamido 2-ethyl propanesulfonic acid and mono-2-(methacryloyloxy)ethylsuccinate. Or aryl/alkyl esters thereof. Or carboxylic anhydride containing monomers such as maleic anhydride; zwitterionic monomers such as (meth)acryloyloxyethyl-phosphoryl choline, quaternised amino monomers such as methacryloyl-oxyethyltrimethyl ammonium chloride.

The corresponding allyl monomer, where applicable, can also be use in each case.

Most preferred monomers are C1-20 alkyacrylates and alkylmethacrylates (linear and branched); arylacrylates and arylmethacrylates, for example benzyl methacrylate; oligomeric acrylic acid esters and oligomeric methacrylic acid esters, for example mono(alk- or aryl-)oxyoligo-[dimethylsiloxane acrylate] and mono(alk- or aryl-)oxyoligo-[dimethylsiloxane methacrylate]; and tri(alkyloxy)-silylalkyl acrylates and tri(alkyloxy)-silylalkyl methacrylates, for example trimethoxysilylpropyl-acrylate and trimethoxysilylpropyl-methacrylate; styrene; α-methyl styrene; vinyl toluene and vinyl acetate.

Hydrophobic monomers include: vinyl aryl compounds such as styrene and vinylbenzyl chloride; acrylic/methacrylic acid esters such as mono-t-butylaminoethyl acrylate/methacrylate, C1-20 alkylacrylates/methacrylates (linear & branched), arylacrylates/methacrylates such as benzyl methacrylate; oligomeric acrylic/methacrylic acid esters such as mono(alk/aryl)oxyoligo-[dimethylsiloxane acrylate/methacrylate] and tri(alkyloxy)-silylalkyl acrylates/methacrylates such as trimethoxysilylpropyl-(meth)acrylate.

Functional monomers, i.e. monomers with reactive pendant groups which can be post or pre-modified with another moiety can also be used such as glycidyl(meth)acrylate, trimethoxysilylpropyl(meth)acrylate, (meth)acryloyl chloride, maleic anhydride, hydroxyalkyl(meth)acrylates, (meth) acrylic acid, vinylbenzyl chloride, activated esters of (meth) acrylic acid such as N-hydroxysuccinamido(meth)acrylate and acetoxystyrene.

The copolymer may contain unreacted polymerisable groups from the multifunctional monomer.

Especially preferred monomers for chain growth polymerisation are: $C_1$-$C_{20}$ linear or branched, alkyl, alkaryl or aryl acrylates and methacrylates.

The Optional Benefit Agent

Advantageously the particle comprises a benefit agent, which is preferably hydrophobic.

As noted above the optional benefit agent may be introduced into the particle during particle formation, or may be introduced into "empty" particles after particle formation.

Various benefit agents may be incorporated into the particles, where they will reside predominantly in the core. Where the end use of the particles is in connection with a surfactant-containing system, any compatible benefit agent which can provide a benefit to a substrate which is treated with a surfactant composition can be used. Advantages of the particles of the invention in the presence of surfactant are a good retention of the benefit agent on storage of a formulation and controllable release of the benefit agent during and after product usage.

Preferred examples include flavours and fragrances, conditioning agents (for example water-insoluble quaternary ammonium materials and/or silicones), sunscreens, colour protection agents, ceramides, antioxidants, dyes, lubricants, unsaturated oils, emollients/moisturiser, insect repellents and/or antimicrobial agents.

For skin compositions the preferred benefit agents include one or more of fragrances, sunscreens, skin lightening agents, antimicrobials, oils and insect repellents. For hair compositions the list of preferred benefit agents is the same with the addition of colour protection agents and dyes.

Preferred antimicrobials include Triclosan™, climbazole, octapyrox, ketoconizole, zinc pyrithione, and quaternary ammonium compounds.

Preferred sunscreens and/or skin lightening agents are vitamin B3 compounds. Suitable vitamin B3 compounds are selected from niacin, niacinamide, nicotinyl alcohol, or derivatives or salts thereof. Other vitamins which act as skin lightening agents can be advantageously included in the skin lightening composition to provide for additional skin lightening effects. These include vitamin B6, vitamin C, vitamin A or their precursors. Mixtures of the vitamins can also be employed in the composition of the invention. An especially preferred additional vitamin is vitamin B6. Other non-limiting examples of skin lightening agents useful herein include adapalene, aloe extract, ammonium lactate, arbutin, azelaic acid, butyl hydroxy anisole, butyl hydroxy toluene, citrate esters, deoxyarbutin, 1,3 diphenyl propane derivatives, 2,5 dihydroxyl benzoic acid and its derivatives, 2-(4-acetoxyphenyl)-1,3 dithiane, 2-(4-Hydroxylphenyl)-1,3 dithiane, ellagic acid, gluco pyranosyl-1-ascorbate, gluconic acid, glycolic acid, green tea extract, 4-Hydroxy-5-methyl-3[2H]-furanone, hydroquinone, 4 hydroxyanisole and its derivatives, 4-hydroxy benzoic acid derivatives, hydroxycaprylic acid, inositol ascorbate, kojic acid, lactic acid, lemon extract, linoleic acid, magnesium ascorbyl phosphate, 5-octanoyl salicylic acid, 2,4 resorcinol derivatives, 3,5 resorcinol derivatives, salicylic acid, 3,4,5 trihydroxybenzyl derivatives, and mixtures thereof. Preferred sunscreens useful in the present invention are 2-ethylhexyl-p-methoxycinnamate, butyl methoxy dibenzoylmethane, 2-hydroxy-4-methoxybenzophenone, octyl dimethyl-p-aminobenzoic acid and mixtures thereof. Particularly preferred sunscreen is chosen from 2-ethyl hexyl-p-methoxycinnamate, 4,-t-butyl-4'-methoxydibenzoyl-methane or mixtures thereof. Other conventional sunscreen agents that are suitable for use in the skin lightening composition of the invention include 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexylsalicylate, glyceryl-p-aminobenzoate, 3,3,5-trimethylcyclohexyl-salicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonic benzoxazoic acid and mixtures of these compounds.

Preferred anti-oxidants include vitamin E, retinol, antioxidants based on hydroxytoluene such as Irganox™ or commercially available antioxidants such as the Trollox™ series.

Perfume and fragrance materials (which include pro-fragrances) are a particularly preferred benefit agent.

The pro-fragrance can, for example, be a food lipid. Food lipids typically contain structural units with pronounced hydrophobicity. The majority of lipids are derived from fatty acids. In these 'acyl' lipids the fatty acids are predominantly present as esters and include mono-, di-, triacyl glycerols, phospholipids, glycolipids, diol lipids, waxes, sterol esters and tocopherols. In their natural state, plant lipids comprise antioxidants to prevent their oxidation. While these may be at least in part removed during the isolation of oils from plants some antioxidants may remain. These antioxidants can be pro-fragrances. In particular, the carotenoids and related compounds including vitamin A, retinol, retinal, retinoic acid and provitamin A are capable of being converted into fragrant species including the ionones, damascones and damscenones. Preferred pro-fragrance food lipids include olive oil, palm oil, canola oil, squalene, sunflower seed oil, wheat germ oil, almond oil, coconut oil, grape seed oil, rapeseed oil, castor oil, corn oil, cottonseed oil, safflower oil, groundnut oil, poppy seed oil, palm kernel oil, rice bran oil, sesame oil, soybean oil, pumpkin seed oil, jojoba oil and mustard seed oil. Perfume components which are odiferous materials are described in further detail below.

The perfume is typically present in an amount of from 10-85% by total weight of the particle, preferably from 15 to 75% by total weight of the particle. The perfume suitably has a molecular weight of from 50 to 500 Dalton. Pro-fragrances can be of higher molecular weight, being typically 1-10 kD.

Useful components of the perfume include materials of both natural and synthetic origin. They include single compounds and mixtures. Specific examples of such components may be found in the current literature, e.g., in Fenaroli's Handbook of Flavour Ingredients, 1975, CRC Press; Synthetic Food Adjuncts, 1947 by M. B. Jacobs, edited by Van Nostrand; or Perfume and Flavour Chemicals by S. Arctander 1969, Montclair, N.J. (USA). These substances are well known to the person skilled in the art of perfuming, flavouring, and/or aromatizing consumer products, i.e., of imparting an odour and/or a flavour or taste to a consumer product traditionally perfumed or flavoured, or of modifying the odour and/or taste of said consumer product.

By perfume in this context is not only meant a fully formulated product fragrance, but also selected components of that fragrance, particularly those which are prone to loss, such as the so-called 'top notes'.

Top notes are defined by Poucher (Journal of the Society of Cosmetic Chemists 6(2):80 [1955]). Examples of well known top-notes include citrus oils, linalool, linalyl acetate, lavender, dihydromyrcenol, rose oxide and cis-3-hexanol. Top notes typically comprise 15-25% wt of a perfume composition and in those embodiments of the invention which contain an increased level of top-notes it is envisaged at that least 20% wt would be present within the particle.

Typical perfume components which it is advantageous to employ in the embodiments of the present invention include those with a relatively low boiling point, preferably those with a boiling point of less than 300, preferably 100-250 Celsius.

It is also advantageous to encapsulate perfume components which have a low LogP (i.e. those which will be partitioned into water), preferably with a LogP of less than 3.0. These materials, of relatively low boiling point and relatively low LogP have been called the "delayed blooming" perfume ingredients and include the following materials:

Allyl Caproate, Amyl Acetate, Amyl Propionate, Anisic Aldehyde, Anisole, Benzaldehyde, Benzyl Acetate, Benzyl Acetone, Benzyl Alcohol, Benzyl Formate, Benzyl Iso Valerate, Benzyl Propionate, Beta Gamma Hexenol, Camphor Gum, Laevo-Carvone, d-Carvone, Cinnamic Alcohol, Cinamyl Formate, Cis-Jasmone, cis-3-Hexenyl Acetate, Cuminic Alcohol, Cyclal C, Dimethyl Benzyl Carbinol, Dimethyl Benzyl Carbinol Acetate, Ethyl Acetate, Ethyl Aceto Acetate, Ethyl Amyl Ketone, Ethyl Benzoate, Ethyl Butyrate, Ethyl Hexyl Ketone, Ethyl Phenyl Acetate, Eucalyptol, Eugenol, Fenchyl Acetate, Flor Acetate (tricyclo Decenyl Acetate), Frutene (tricycico Decenyl Propionate), Geraniol, Hexenol, Hexenyl Acetate, Hexyl Acetate, Hexyl Formate, Hydratropic Alcohol, Hydroxycitronellal, Indone, Isoamyl Alcohol, Iso Menthone, Isopulegyl Acetate, Isoquinolone, Ligustral, Linalool, Linalool Oxide, Linalyl Formate, Menthone, Menthyl Acetphenone, Methyl Amyl Ketone, Methyl Anthranilate, Methyl Benzoate, Methyl Benyl Acetate, Methyl Eugenol, Methyl Heptenone, Methyl Heptine Carbonate, Methyl Heptyl Ketone, Methyl Hexyl Ketone, Methyl Phenyl Carbinyl Acetate, Methyl Salicylate, Methyl-N-Methyl Anthranilate, Nerol, Octalactone, Octyl Alcohol, p-Cresol, p-Cresol Methyl Ether, p-Methoxy Acetophenone, p-Methyl Acetophenone, Phenoxy Ethanol, Phenyl Acetaldehyde, Phenyl Ethyl Acetate, Phenyl Ethyl Alcohol, Phenyl Ethyl Dimethyl Carbinol, Prenyl Acetate, Propyl Bornate, Pulegone, Rose Oxide, Safrole, 4-Terpinenol, Alpha-Terpinenol, and/or Viridine It is commonplace for a plurality of perfume components to be present in a formulation. In the encapsulates of the present invention it is envisaged that there will be four or more, preferably five or more, more preferably six or more or even seven or more different perfume components from the list given of delayed blooming perfumes given above present in the particles.

Another group of perfumes with which the present invention can be applied are the so-called 'aromatherapy' materials. These include many components also used in perfumery, including components of essential oils such as Clary Sage, *Eucalyptus*, Geranium, Lavender, Mace Extract, Neroli, Nutmeg, Spearmint, Sweet Violet Leaf and Valerian.

The volatile benefit agents also include insect repellent materials (where insect should be read broadly to include other pests which are arthropods but not strictly hexapods— for example ticks). Many of these materials overlap with the class of perfume components and some are odourless to humans or have a non-perfume odour. Commonly used repellents include: DEET (N,N-diethyl-m-toluamide), essential oil of the lemon *eucalyptus* (*Corymbia citriodora*) and its active compound p-menthane-3,8-diol (PMD), Icaridin, also known as Picaridin, D-Limonene, Bayrepel, and KBR 3023, Nepetalactone, also known as "catnip oil", Citronella oil, Permethrin, Neem oil and Bog Myrtle. Known insect repellents derived from natural sources include: *Achillea alpina*, alpha-terpinene, Basil oil (*Ocimum basilicum*), *Callicarpa americana* (Beautyberry), Camphor, Carvacrol, Castor oil (*Ricinus communis*), Catnip oil (*Nepeta* species), Cedar oil (*Cedrus atlantica*), Celery extract (*Apium graveolens*), Cinnamon (*Cinnamomum* Zeylanicum, leaf oil), Citronella oil (*Cymbopogon fleusus*), Clove oil (*Eugenic caryophyllata*), *Eucalyptus* oil (70%+ eucalyptol, also known as cineol), Fennel oil (*Foeniculum vulgare*), Garlic Oil (*Allium sativum*), Geranium oil (also known as *Pelargonium graveolens*), Lavender oil (*Lavandula officinalis*), Lemon *eucalyptus* (*Corymbia citriodora*) essential oil and its active ingredient p-menthane-3,8-diol (PMD), Lemongrass oil (*Cymbopogon flexuosus*), Marigolds (*Tagetes* species), Marjoram (*Tetranychus urticae* and *Eutetranychus orientalis*), Neem oil (*Azadirachta indica*), Oleic acid, Peppermint (*Mentha x piperita*), Pennyroyal (*Mentha pulegium*), Pyrethrum (from *Chrysanthemum* species, particularly *C. cinerariifolium* and *C. coccineum*), Rosemary oil (*Rosmarinus officinalis*), Spanish Flag Lantana camara (*Helopeltis theivora*), *Solanum villosum* berry juice, Tea tree oil (*Melaleuca alternifolia*) and Thyme (*Thymus* species) and mixtures thereof.

Preparation Methods

Polymerisation occurs in at least three phases, in which the shells and the core are formed.

The core is formed first and the shell is deposited onto the core. This method is followed in the examples given below.

Temporal separation of these phases is accomplished by control of the reagents present and the reaction conditions.

Typically, at least one of the components of the shell-forming reaction is withheld from the initial reaction mixture and added gradually to control the progress of the reaction in the first phase.

The preferred method is one in which an emulsion is formed comprising the step-growth polymer components are at the interface between the dispersed phase and the continuous aqueous phase.

Typically the aqueous phase comprises an emulsifying agent and a co-monomer.

The disperse phase comprises the chain-growth monomer, the initiator, the other co-monomer for the step growth polymer and any optional benefit agent.

A preferred method of preparation of the particles comprises the following steps:— a) forming an emulsion, preferably having a mean dispersed particle size diameter of less than 1000 nm, more preferably less than 500 nm and having a dispersed non-aqueous phase comprising:
  i) a first inner shell co-monomer, capable of step-growth polymeriation with a suitable second inner shell co-monomer,
  ii) an optional benefit agent, preferably an organoleptic benefit agent,
  iii) at least one outer shell monomer, preferably acrylate or methacrylate, capable of chain-growth polymerisation, and iv) a radical initiator, preferably peroxide or azo-, which is not significantly active at the temperature at which the first inner shell co-monomer undergoes step-growth polymerisation and a continuous aqueous phase comprising:
I) water,
II) an emulsifying agent,
III) a second inner shell co-monomer for the first inner shell co-monomer, preferably a diol or diamine, b) polymerising the first and second inner shell co-monomers to form an inner shell polymer with a glass transition temperature above 70 degrees Celsius, preferably above 80 degrees Celsius;

c) adding an outer shell monomer and a deposition aid and polymerising to form an outer shell having a glass transition temperature of below 35 Celcius having a covalently bound deposition aid.

The inner shell is formed from the first and second inner shell co-monomers and the outer shell is formed from the outer shell monomer.

Advantageously, the above described method provides a potentially "one-pot" reaction which has the advantages of simplicity and reduced losses: i.e. the shell is formed by step-growth polymerisation at the interface of the emulsion droplets and the core is subsequently formed within the shell by an in-situ chain-growth polymerisation.

The optional benefit agent may be present in the reaction mixture, at a level to give the benefit agent levels in the resulting particles at the levels disclosed above, although it is also possible to form "empty" particles and subsequently expose them to a benefit agent which can be adsorbed into the inner region.

Surface modification materials are generally added to the aqueous phase towards the end of the process, where, for example, further monomer(s) can be added to form further shell material and bind additional materials to the outside of the particle.

Particles according to the present invention may be formed from an emulsion by carrying out an interfacial step-growth polymerisation first to form a shell under conditions where the chain-growth polymerisation is inhibited. Subsequently, the conditions are changed such that the material within the shell undergoes the chain-growth polymerisation. A suitable change in conditions is to increase the temperature from one at which the chain growth reaction is inhibited to one at which it proceeds. Other possible changes of conditions would be, for example, to use a chain-growth reaction which is light dependent rather than temperature dependent.

Emulsifying Agents

Many emulsifying agents are known for use in emulsion polymerisation. Suitable emulsifying agents for use in the polymerisation process may comprise, but are not limited to, non-ionic surfactants such as polyvinylpyrrolidone (PVP), polyethylene glycol sorbitan monolaurate (Tween 20), polyethylene glycol sorbitan monopalmitate (tween 40), polyethylene glycol sorbitan monooleate (Tween 80), polyvinyl alcohol (PVA), and poly(ethoxy)nonyl phenol, ethylene maleic anhydride (EMA) copolymer, Easy-Sperse™ (from ISP Technologies Inc.), ionic surfactants such as partially neutralized salts of polyacrylic acids such as sodium or potassium polyacrylate or sodium or potassium polymethacrylate. Brij™-35, Hypermer™ A 60, or sodium lignosulphate, and mixtures thereof.

Emulsifiers may also include, but are not limited to, acrylic acid-alkyl acrylate copolymer, poly(acrylic acid), polyoxyalkylene sorbitan fatty esters, polyalkylene co-carboxy anhydrides, polyalkylene co-maleic anhydrides, poly(methyl vinyl ether-co-maleic anhydride), poly(propylene-co-maleic anhydride), poly(butadiene co-maleic anhydride), and poly (vinyl acetate-co-maleic anhydride), polyvinyl alcohols, polyalkylene glycols, polyoxyalkylene glycols, and mixtures thereof.

Preferred emulsifying agents are fatty alcohol exthoylates (particularly of the Brij™ class), salts of ether sulphates (including SLES), alkyl and alkaryl sulphonates and sulphates (including LAS and SDS) and cationic quaternary salts (including CTAC and CTAB).

The nature of the emulsifying agent can be selected to ensure that the finished particle is compatible with the environment in which it will be used. In particular cores which are formed in the presence of anionic surfactant systems (for example SLES 1-4 EO, preferably 1-3 EO and the others mentioned above) are compatible with products in which the environment comprises an anionic surfactant, such as, for example body-wash products and shampoos. Cores which are formed in the presence of cationic surfactant (for example a cationic quaternary salt as mentioned above and in particular one of the alkyl trimethyl ammonium halides) are compatible with products in which the environment comprises a cationic surfactant, for example a hair conditioner.

It is particularly preferred that the emulsifying agent further comprises a nonionic surfactant. This is believed to produce a particle which deposits better on skin or hair than one produced solely with a charged surfactant emulsifier. It is also preferred that the non-ionic surfactant is hydrophilic, so as to promote the formation of a stable mini-emulsion. The alcohol ethoxylates with more than ten moles of ethoxylation, for example Synperonic A20 (C1320EO), yield good results. DLS data for samples shows that as the level of surfactant increases the particle size becomes smaller, which is also advantageous. Preferably, the ratio of non-ionic to anionic emulsifier should be greater than 1:1 (i.e. non-ionic is present in excess) and the total surfactant level should be >3% wt of the polymerisation mixture.

Co-Surfactant:

Typically a co-surfactant will be present in the dispersed phase and in the resulting particle. Suitable co-surfactants for use in the present invention include hexadecane, cetyl alcohol, lauroyl peroxide, n-dodecyl mercaptan, dodecyl methacrylate, stearyl methacrylate, polystyrene, polydecene, mineral oils, isopropyl myristate $C_{13}$-$C_{15}$ alkyl benzoate and polymethyl methacrylate.

The preferred cosurfactants comprise hexadecane, polydecene and isopropyl myristate.

As a wt % of oil phase as a total, the co-surfactant is typically 0-20%, preferably 1-15%, more pref 2-12.5%.

Polymerisation Conditions

Typically the polymerisation temperature is about 70 Celcius, typically 70-95 Celcius.

Deposition aid may added with the outer shell forming material to bind the deposition aid to the outer surface of the particle by the formation of further shell material which entraps a portion of the deposition aid and leads to a "hairy" particle in which the "hair" comprises the deposition aid.

For simple core-shell particles, the core excluding benefit agent is less than or equal to 80% wt of mass, and the shell generally 20% wt or greater of the mass of the particle.

Preferably the emulsion polymerisation step is a so-called "mini-emulsion" polymerisation, performed with a dispersed phase droplet size of below one micron. Sufficiently fine emulsions can be obtained by a range of methods, including sonication, and/or via high shear dynamic mixers or static mixers. Mini-emulsion products have excellent suspending properties.

A preferred particle of the invention is a particle comprising:
- a) a core, comprising
  - i) a polymer having a glass transition temperature below 30 Celsius, and,
  - ii) at least one perfume component
- b) a water-insoluble, poly($C_1$-$C_4$ methacrylate) inner shell surrounding the core, said inner shell having a glass transition temperature which is above 80 Celsius,
- c) a water insoluble poly($C_1$-$C_4$ acrylate) outer shell at least partially surrounding said inner shell, said outer shell having a glass transition temperature below zero Celsius, and,
- d) a deposition aid, which is substantive to cotton and which is attached to the outer shell and not removed by exposure to water, said deposition aid including at least one polysaccharide selected from the group consisting of poly-mannan, poly-glucan, poly-glucomannan, poly-xyloglucan, poly-galactomannan, dextran, hydroxyl-propyl cellulose, hydroxy-propyl methyl cellulose, hydroxy-ethyl methyl cellulose, hydroxy-propyl guar, hydroxy-ethyl ethyl cellulose or methyl cellulose.

Use in Products

The end-product compositions of the invention may be in any physical form e.g., a solid bar, a paste, gel or liquid, especially, an aqueous-based liquid.

The particles of the invention may be advantageously incorporated into surfactant-containing compositions. The particles are typically included in said compositions at levels of from 0.001% to 10%, preferably from 0.005% to 7.55%, most preferably from 0.01% to 5% by weight of the total composition.

A product comprising the particles of the invention may be prepared by adding the particles and the benefit agent to a formulation, separately.

Formulated compositions comprising the particles of the invention may contain a surface-active compound (surfactant) which may be chosen from soap and non-soap anionic, cationic, non-ionic, amphoteric and zwitterionic surface active compounds and mixtures thereof. Many suitable surface active compounds are available and are fully described in the literature, for example, in "Surface-Active Agents and Detergents", Volumes I and II, by Schwartz, Perry and Berch. The preferred surface-active compounds that can be used are soaps and synthetic non soap anionic, and non-ionic compounds.

Suitable anionic surfactants are well-known to those skilled in the art. Examples include primary and secondary alkyl sulphates, particularly C8 to C15 primary alkyl sulphates; alkyl ether sulphates; olefin sulphonates; alkyl xylene sulphonates; dialkyl sulphosuccinates; and fatty acid ester sulphonates. Sodium salts are generally preferred.

Compositions may also contain non-ionic surfactant. Non-ionic surfactants that may be used include the primary and secondary alcohol ethoxylates, especially the C8 to C20 aliphatic alcohols ethoxylated with an average of from 1 to 20 moles of ethylene oxide per mole of alcohol, and more especially the C10 to C15 primary and secondary aliphatic alcohols ethoxylated with an average of from 1 to 10 moles of ethylene oxide per mole of alcohol. Non ethoxylated nonionic surfactants include alkylpolyglycosides, glycerol monoethers, and polyhydroxyamides (glucamide).

It is preferred if the level of non-ionic surfactant is from 0 wt % to 30 wt %, preferably from 1 wt % to 25 wt %, most preferably from 2 wt % to 15 wt %, by weight of a fully formulated composition comprising the particles of the invention. The particles of the invention are particularly used in compositions that are used in an aqueous environment comprising a rinse, for the treatment of textiles, hair and skin.

A home or personal care composition comprising at least one particle according to the invention is advantageously a deodorant, antiperspirant, shampoo, hair conditioner or skin care or skin cleansing product.

A composition comprising particles of the invention may be used in a method of treatment of a substrate, which includes the step of treating the substrate with the composition. The substrate is preferably selected from skin and hair,

EXAMPLES

Example 1

Synthesis of a Typical "Core Particle"; P1

A surfactant solution was prepared by dissolving 4.09 g Rhodasurf B7 (Rhodia) and 0.84 g sodium dodecyl sulfate in 285 ml demin water.

6.38 g of hexadecane, 166.8 g of butyl methacrylate monomer were weighed into a 500 ml jar and the mixture gently shaken to form a crude emulsion.

Using a sonic probe (Branson Digital Sonfier 450D), the crude emulsion was ultrasonicated at 50% amplitude for 5 min. The jar was sealed and shaken and the emulsion ultrasonicated at 50% amplitude for a further 5 min.

The miniemulsion was transferred into a 1000 mL 3-neck round bottom flask fitted with a condenser and an overhead stirrer and heated to 80° C.

Once at the desired temperature the first part of the initiation system was added, 1.68 g sodium bicarbonate in 20 mL water.

The second part of the initiation system (1.68 g ammonium persulfate in 10 ml water) was added dropwise over a 45 minute period.

Once the addition had finished the reaction mixture was stirred for 90 minutes and subsequently allowed to cool.

The reaction vessel and stirrer were checked for signs of coagulation and grit formation.

Final solids content was determined by gravimetric analysis and the particle size determined by dynamic light scattering. (35% solids and 165 nm particle size.)

Example 2

Addition of an "Inner" Polymeric Shell (Having a Tg of Greater than 70 Celcius) to the "Core Particle" of Example 1 to Form a "Core-Shell Particle"; P2

285 g polymer particle dispersion prepared via example 1 was transferred to a 1 L 3-neck reaction flask.

215 g demin water was added and the flask fitted with an overhead stirrer and condenser.

The emulsion was then heated to 80° C. with stirring at 300 rpm.

Initiator solutions were prepared by dissolving 0.225 g ammonium persulfate in 2 ml water and 0.225 g sodium bicarbonate in 4 ml water and added via pipette.

The shell monomer, 15 g methyl methacrylate, was added dropwise via syringe pump over the course of 60 minutes. After complete monomer addition, the reaction was stirred for a further 1.5 hours.

0.075 g Ascorbic acid in 2 mL water and 0.075 g t-butylhydroperoxide were added subsequently, and the reaction allowed to stir for a further 30 minutes after which, the reaction was cooled to room temperature and filtered through BioPrepNylon synthetic cheesecloth (50 µm).
The reaction vessel and stirrer were checked for signs of coagulation and grit formation.
Final solids content was determined by gravimetric analysis and the particle size determined by dynamic light scattering. (21.6% solids and 195 nm particle size.)

Example 3

Addition of Deposition Aid and an Outer Shell to the "Core Particle" of Example 1 (to Form P3) and to the "Core-Shell Particle" of Example 2 (to Form P4i)

Particle P4i is in accordance with the invention.
150 g polymer particle dispersion from example 2 or 85.7 g polymer from example 1 and 64.3 g demin water were added to a 500 ml 3-neck reaction flask fitted with an overhead stirrer and condenser.
0.5 g polysaccharide (eg. Locust bean gum) was dissolved in 49.5 ml boiling water using a IKA T25 homogenizer at 12,000 rpm for 2 minutes.
32 g polysaccharide solution was added to the 500 ml flask and the emulsion heated to 75° C. and stirred for 30 minutes at 250 rpm.
0.18 g ascorbic acid was dissolved in 2 ml water and added via pipette and then methyl acrylate (1.7 ml) followed by 30% hydrogen peroxide (0.45 ml) were added and the mixture stirred for 2 hours.
30% hydrogen peroxide solution (0.1 ml) and ascorbic acid (0.04 g) in 0.5 ml water were then added and stirred for a further two hours.
The reaction was allowed to cool, and transferred to a jar.
The reaction vessel and stirrer were checked for signs of coagulation and grit formation.
Final solids content was determined by gravimetric analysis and the particle size determined by dynamic light scattering. (Example 1 core only=19.0% solids and 206 nm particle size, Example 2 core-shell=19.6% solids and 223 nm particle size.)
In this way, the following particles shown in Table 1 were prepared:—

TABLE 1

Composition of Particles P3 and P4i.

| Component | P3 | P4i |
|---|---|---|
| Polymer particle dispersion from Example 1 (P1) | 85.7 g | — |
| Polymer particle dispersion from Example 2 (P2) | — | 150 g |
| Demin water | 64.3 g | — |
| 1% Locust Bean Gum Solution | 32 g | 32.0 g |
| Methyl Acrylate | 1.62 g | 1.62 g |
| 30% Hydrogen Peroxide solution | 0.55 ml | 0.55 ml |
| Ascorbic Acid | 0.22 g in 2.5 ml water | 0.22 g in 2.5 ml water |

Example 4

Particle Deposition Using the Particles P3 and P4i

Deposition of the particles P3 (outside the invention) and P4i (in accordance with the invention) onto fabric during a laundry wash process was measured using the procedure outlined below:—

Particle deposition during washing was measured by turbidity as follows:
a) Preparation of Stock Solutions:
   Surfactant Stock: (10 g/L 50:50 LAS:A7) was prepared by dissolving Linear Alkyl Benzene Sulphonate (9.09 g LAS (55% Active)) and Synperonic A7 (5 g) in de-ionised water to a total of 1 liter.
   Base Buffer Stock: (0.1 M) was prepared by dissolving Sodium Carbonate (7.5465 g) and Sodium Hydrogen Carbonate (2.4195 g) in de-ionised water to a total of 1 liter.
b) Preparation of the Wash Liquor:
   Base Buffer Stock (10 ml) and surfactant stock (10 ml) were added to a 500 ml Linitest pot and 80 ml de-ionised water was added to produce a wash liquor buffered at pH 10.5 and containing 1 g/L surfactant (50:50 LAS:A7).
c) Simulated Wash:
   0.04 g (400 ppm on wash liquor) of polymer particles were used. The capsules were added to the linitest pots containing wash liquor and agitated slightly to ensure mixing. Washes were done in duplicate for each sample and results averaged. A 5 ml aliquot was taken from each and the Absorbance at 400 nm recorded using a 1 cm cuvette. This absorbance value represents 100% particles in the wash solution prior to the simulated wash process.
d) Linitest Equipment and Procedure:
   Linitest™ laboratory scale washing machines (Ex. Heraeus), having a single rotation speed of 40 rpm were employed. A section of unfluoresced cotton (or knitted polyester as appropriate) measuring 20 cm by 20 cm was placed into each Linitestpot containing the wash liquor and polymer particles and the pot was sealed. The Linitest pots were then attached to the Linitester cradle and rotated 45 minutes at 40 Celcius to simulate the main wash.
   The cloths were then removed, wrung by hand and a 5 ml aliquot of the remaining wash liquor was taken and the absorbance at 400 nm measured using a 1 cm cuvette. From interpolation of the initial calibration curve, the concentration of the particles remaining the liquor after the wash could be determined and hence the level deposited (wash deposition) on the cloth could be determined by difference.
   The Linitest pots were then thoroughly rinsed and the 'wrung' cloths returned to the pots and 125 ml of de-ionised water was added. The Linitester bath water was drained and the pots attached to the cradle and rotated for 10 minutes at ambient temperature (~20 Celcius) to simulate a rinse procedure. The clothes were then removed and wrung by hand. A 5 ml aliquot of the rinse solution was taken and the absorbance at 400 nm determined. Interpolation of the initial calibration plot allowed the particle concentration removed from the cloth during the rinse to be determined and by comparison to the initial level deposited prior to the rinse, the percentage loss from the cloth could be determined. This procedure was repeated to simulate and determine losses from subsequent rinses.
   The results obtained were as follows:

TABLE 2

Deposition (%) of particle P3 and P4i onto fabric during a wash process.

|  | P3 | P4i |
|---|---|---|
| Wash | 47.3% | 95.6% |
| Rinse 1 | 32.4% | 69.0% |
| Rinse 2 | 18.8% | 46.0% |

It will be seen that increased deposition is achieved by adding a glassy inner shell before the outer shell and deposition aid. Surprisingly, the glassy inner shell is key in obtaining high deposition.

Example 5

Particles P5i, P6i and P11i in Accordance with the Invention, and Comparative Particles P7-P10 and P12, Comprising Outer Shells Having Different Glass Transition Temperatures Samples were prepared as detailed below using the method outlined in Example 3.

TABLE 3

Composition of Particles P5i, P6i and P11i in accordance with the invention, and Comparative Particles P7-P10 and P12, comprising an outer shell having a range of glass transition temperatures.

| | P5i | P6i | P7 | P8 | P9 | P10 | P11i | P12 |
|---|---|---|---|---|---|---|---|---|
| Polymer particle dispersion from Example 2 (P2) | 150 g | 150 g | 150 g | 150 g | 150 g | 150 g | 150 g | 150 g |
| 1% Locust Bean Gum Solution | 32.0 g | 32.0 g | 32.0 g | 32.0 g | 32.0 g | 32.0 g | 32.0 g | 32.0 g |
| Methyl Acrylate | 1.62 g | — | — | — | — | — | — | — |
| Ethyl Acrylate | — | 1.62 g | — | — | — | — | — | — |
| Butyl Acrylate | — | — | 1.62 g | — | — | — | — | — |
| Ethylhexyl Acrylate | — | — | — | 1.62 g | — | — | — | — |
| Methyl Methacrylate | — | — | — | — | 1.62 g | — | — | — |
| Butyl Methacrylate | — | — | — | — | — | 1.62 g | — | — |
| Vinyl Acetate | — | — | — | — | — | — | 1.62 g | — |
| Styrene | — | — | — | — | — | — | — | 1.62 g |
| 30% Hydrogen Peroxide solution | 0.55 ml | 0.55 ml | 0.55 ml | 0.55 ml | 0.55 ml | 0.55 ml | 0.55 ml | 0.55 ml |
| Ascorbic Acid (in 2.5 ml water) | 0.22 g | 0.22 g | 0.22 g | 0.22 g | 0.22 g | 0.22 g | 0.22 g | 0.22 g |
| Tg/° C. | 8 | −22 | −54 | −85 | 105 | 20 | 30 | 100 |

Example 6

Deposition of these Particles onto Fabric During a Wash Process

The resulting polymers were subjected a laundry deposition test using the procedure outlined above. The results obtained were as follows:

TABLE 4

Deposition (%) of particles P5i-P12 onto fabric during a wash process.

| | P5i | P6i | P7 | P8 | P9 | P10 | P11i | P12 |
|---|---|---|---|---|---|---|---|---|
| Wash | 95.6 | 47.8 | 0 | 1.6 | 0 | 0.9 | 38.5 | 2.5 |
| Rinse 1 | 69.0 | 30.2 | 0 | 1.3 | 0 | 0.8 | 24.9 | 1.2 |
| Rinse 2 | 46.0 | 22.6 | 0 | 1.2 | 0 | 0.7 | 18.7 | 0.8 |

It will be seen that particles in accordance with the invention give dramatically improved deposition onto fabric. Butyl methacrylate, with a solubility of only 3 g/L water at STP does not give rise to acceptable deposition, despite its glass transition temperature.

The invention claimed is:

1. A particle comprising:
   a) a core, comprising an optional benefit agent;
   b) an inner shell at least partially surrounding the core, said inner shell being the water insoluble product of a polymerisation reaction to form a first polymer with a glass transition temperature above and including 70 degrees Celsius;
   c) an outer shell at least partially surrounding said inner shell, said outer shell being the water insoluble product of a polymerisation reaction to form a second polymer with a glass transition temperature below and including 35 degrees Celsius, wherein the second polymer is formed from a monomer having a solubility in water of greater than 3 g/L at STP; and
   d) a deposition aid, covalently attached to the outer shell.

2. A particle according to claim 1, wherein at least one of the first and second polymers are formed from ethylenically-unsaturated monomers.

3. A particle according to claim 1, wherein the first polymer is an acrylic glass.

4. A particle according to claim 1, wherein the second polymer has a glass transition temperature of from minus 50 to +25 Celcius.

5. A particle according to claim 1, wherein the second polymer is a poly($C_1$-$C_4$ acrylate).

6. A particle according to claim 1, wherein the second polymer is formed from a monomer having a solubility in water of greater than and including 10 g/L at STP.

7. A particle according to claim 1, wherein the deposition aid is a polysaccharide.

8. A particle according to claim 7, wherein the deposition aid is selected from the group consisting of poly-mannan, poly-glucan, poly-glucomannan, poly-xyloglucan, poly-galactomannan, dextran, hydroxyl-propyl cellulose, hydroxy-propyl methyl cellulose, hydroxy-ethyl methyl cellulose, hydroxy-propyl guar, hydroxy-ethyl ethyl cellulose, methyl cellulose and mixtures thereof.

9. A particle according to claim 1, wherein the inner shell has a glass transition temperature of from 80 to 115 Celcius.

10. A particle according to claim 1 wherein the core comprises at least one perfume component.

11. The particle according to claim 1 wherein the glass transition temperature of the first polymer is above and including 80° C.

12. The particle according to claim 3 wherein the first polymer is poly(methyl methacrylate).

13. The particle according to claim 5 wherein the second polymer is poly(methyl acrylate).

14. The particle according to claim 9 wherein the inner shell has a glass transition temperature from 90 to 110 Celcius.

15. A home or personal care composition comprising at least one particle according to claim 1, wherein the composition is selected from the group consisting of a deodorant, antiperspirant, shampoo, hair conditioner and skin care or skin cleansing product.

16. A core-shell benefit agent carrier particle comprising:
   a) a core, comprising
      i) a polymer having a glass transition temperature below 30 Celsius, and,
      ii) at least one perfume component
   b) a water-insoluble, poly($C_1$-$C_4$ methacrylate) inner shell surrounding the core, said inner shell having a glass transition temperature which is above 80 Celsius,
   c) a water insoluble poly($C_1$-$C_4$ acrylate) outer shell at least partially surrounding said inner shell, said outer shell having a glass transition temperature below zero Celsius, and,
   d) a deposition aid, which is attached to the outer shell and not removed by exposure to water, said deposition aid including at least one polysaccharide selected from the group consisting of poly-mannan, poly-glucan, poly-glucomannan, poly-xyloglucan, poly-galactomannan, dextran, hydroxyl-propyl cellulose, hydroxy-propyl methyl cellulose, hydroxy-ethyl methyl cellulose, hydroxy-propyl guar, hydroxy-ethyl ethyl cellulose or methyl cellulose.

17. A method of treatment of a substrate, wherein the substrate is selected from skin and/or hair, which includes the step of treating the substrate with a composition comprising particles according to claim 1.

* * * * *